(12) United States Patent
Veneruso et al.

(10) Patent No.: US 9,116,105 B2
(45) Date of Patent: Aug. 25, 2015

(54) WATER FRACTION MEASURING SENSOR AND METHOD HAVING CAPACITANCE MODULE

(75) Inventors: Anthony Veneruso, Sugar Land, TX (US); Christian Chouzenoux, Saint Cloud (FR); Yann Dufour, Vanves (FR); José Teixeira, Chaville (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 660 days.

(21) Appl. No.: 13/147,617

(22) PCT Filed: Feb. 27, 2010

(86) PCT No.: PCT/IB2010/050858
§ 371 (c)(1),
(2), (4) Date: Oct. 3, 2011

(87) PCT Pub. No.: WO2010/097782
PCT Pub. Date: Sep. 2, 2010

(65) Prior Publication Data
US 2012/0041681 A1    Feb. 16, 2012

(30) Foreign Application Priority Data
Feb. 26, 2009   (EP) .................................. 09153710

(51) Int. Cl.
| | | |
|---|---|---|
| *G01V 1/40* | (2006.01) | |
| *G01N 27/22* | (2006.01) | |
| *E21B 47/10* | (2012.01) | |
| *G01N 33/28* | (2006.01) | |

(52) U.S. Cl.
CPC ............ *G01N 27/223* (2013.01); *E21B 47/102* (2013.01); *G01N 33/2823* (2013.01)

(58) Field of Classification Search
CPC ............ G01N 33/2847; G01N 27/223; G01N 33/2823; E21B 47/102; G01F 1/44; G01F 1/74
USPC ............................................................ 702/13
See application file for complete search history.

(56) References Cited

U.S. PATENT DOCUMENTS

| | | | |
|---|---|---|---|
| 3,721,121 A |   | 3/1973 | Fierfort |
| 4,073,712 A | * | 2/1978 | Means et al. .................. 204/554 |
| 5,526,696 A | * | 6/1996 | Cappi ........................ 73/861.95 |
| 2003/0011386 A1 | * | 1/2003 | Xie et al. ....................... 324/694 |
| 2005/0264302 A1 | * | 12/2005 | Mohajer et al. ............... 324/639 |
| 2009/0288838 A1 | * | 11/2009 | Richards ....................... 166/374 |

FOREIGN PATENT DOCUMENTS

| | | |
|---|---|---|
| FR | 2193929 | 2/1974 |
| GB | 2209286 | 5/1989 |

* cited by examiner

*Primary Examiner* — Elias Desta
(74) *Attorney, Agent, or Firm* — Cameron R. Sneddon; Robert A. Van Someren (57) ABSTRACT

A sensor for measuring water fraction in a fluid mixture flowing in a conductive tubing within a borehole. The sensor comprises: an active probe, a reference probe, and an electronic unit. The active probe includes a first electrode and a second electrode isolated from each other by a first insulating layer, the first and second electrodes are preferably in contact with the fluid mixture. The reference probe is formed from an internal wall of the conductive tubing contacting the fluid mixture and isolated from the reference probe by a second insulating layer. The electronic unit is coupled to the first and second electrodes, and to the reference probe, the electronic unit preferably includes a capacitance module for measuring a capacitance between the active probe and the reference probe.

15 Claims, 6 Drawing Sheets

WATER FRACTION MEASURING SENSOR AND METHOD HAVING CAPACITANCE MODULE

CROSS-REFERENCE TO RELATED APPLICATION

The present application is based on and claims priority to PCT application PCT/IB2010/050858, which claims priority to European Patent Application No. EP09153710, filed Feb. 26, 2009, the contents of all being expressly incorporated herein by reference.

BACKGROUND

1. Technical Field

An aspect of the present invention relates to a sensor for measuring water fraction in a fluid mixture, and more particularly, but not by way of limitation, to a fluid mixture flowing in a borehole of a hydrocarbon well.

2. Background Art

At various moments in the lifetime of a hydrocarbon well, it is important to identify downhole reservoir zones, and in particular the fraction of water produced relative to the hydrocarbon fluid (e.g., oil, gas). Water production and disposal from hydrocarbon fluid production are costly operations and may be have ecological drawbacks. Thus, early identification enables taking quick appropriate remedial action.

During drilling operations and shortly after a hydrocarbon well has been drilled, the water fraction in the fluid mixture flowing from the geological formation into the borehole may be measured, for example, by running a wireline sonde. This enables identifying zones that produce excessive water. After completion operations and after production operations have begun, making water fraction measurements by running a wireline sonde is prohibitively expensive or technically impractical due to the presence of completion/production equipments like packers, production tubings, etc. Further, hydrocarbon wells equipped with a sub-sea well head or having a long horizontal producing section cannot be logged in a conventional or cost effective manner.

It is known to deploy permanent sensors for measuring oil and water fraction at the reservoir level. Measuring tools may be deployed into a well to form an array. However, this has not been commercially viable due to the complexity of the tools and the high capital investment.

Furthermore, it is known in the art to measure water fraction in a fluid mixture flowing into a conductive pipe by measuring the capacitance between two plates or electrodes in direct contact with the fluid mixture. The two plates are manufactured as thin layers of metal and are electrically insulated from the conductive pipe. In harsh downhole environment encountered in the oilfield industry, the conductive pipe is made of steel or other metal alloy in order to resist the surrounding wellbore pressure and chemical aggression. It is difficult to maintain the electrodes on the inner face of the conductive pipe and electrically insulate each electrode from the pipe. In particular, the insulation cannot withstand downhole conditions over a long period of time.

SUMMARY OF THE INVENTION

It is an object of the present invention to propose a sensor to measure water fraction in a fluid mixture flowing into a borehole, or a water fraction measuring method that overcomes one or more of the limitations of the existing water fraction measuring sensor or method.

According to one aspect of the present invention there is provided a sensor for measuring water fraction in a fluid mixture flowing in a conductive tubing within a borehole, wherein the sensor comprises: an active probe having a first electrode and a second electrode isolated from each other by a first insulating layer, the first and second electrodes being in contact with the fluid mixture; a reference probe formed from an internal wall of the conductive tubing contacting the fluid mixture and isolated from the reference probe by a second insulating layer; and an electronic unit coupled to the first and second electrodes, and to the reference probe, the electronic unit having a capacitance module for measuring a capacitance between the active probe and the reference probe.

According to an optional aspect, the first and second insulating layer coats the first and second electrode, respectively, such that the first and second electrodes contacts the fluid mixture at a distal part of the electrodes.

The active probe and/or the reference probe may be coated by a protector layer cap. The fluid mixture is a hydrocarbon fluid mixture.

The sensor may be further coupled to a mixing device for mixing the fluid mixture before contacting the active probe. The mixing device may be a helix or a restriction to the flow cross-section forming a Venturi throat.

The electronic unit may further comprise a transmission module to transfer measurements to surface equipments.

The conductive tubing may be an instrumented tubing connectable outside a production tubing, a first end of the instrumented tubing being open, a second end of the instrumented tubing being closed, the instrumented tubing comprising a lateral hole adapted to direct the fluid mixture in the production tubing.

According to another aspect, the present invention relates to a production controlling system of a producing zone of a hydrocarbon well comprising a water fraction in a fluid mixture measuring sensor according to the present invention. The system comprises a valve to choke the producing zone, the valve being coupled to the sensor, the sensor operating the valve as a function of the measured water fraction in the fluid mixture produced by the producing zone and a threshold water fraction value.

According to yet a further aspect, the present invention relates to a method of measuring water fraction in a fluid mixture flowing in a conductive tubing within a borehole comprising: measuring the water fraction with a sensor having an active probe in contact with the fluid mixture; coupling the sensor to the conductive tubing such that an internal wall in contact with the fluid mixture forms a reference probe; and measuring a capacitance between the active probe and the reference probe.

According to optional aspect, the water fraction in the fluid mixture is calculated by determining the dielectric constant of the fluid mixture surrounding the active probe from the capacitance measurement.

The water fraction $H_w$ in the fluid mixture is calculated by using the Bruggeman formula.

According to still a further aspect, the present invention relates to an application of the method of the present invention to the control of production of a hydrocarbon reservoir, comprising the steps of: measuring the water fraction in the fluid mixture of a producing zone, and operating a valve to choke the producing zone when the measured water fraction in the fluid mixture exceeds a threshold value.

Thus, the sensor avoids the need to insulate the conductive tubing because the conductive tubing is used as a reference probe.

The sensor is simple, reliable over time, cost effective and provides accurate estimation of water and oil fraction. The sensor has a high sensitivity to water fraction.

It may be used in permanent application while enabling a minimum impact on the well completion. In effect, its miniaturization renders the sensor suitable for placement in borehole, and its reliability enables long lifetime function according to determined specifications in harsh downhole environments (high pressure and/or temperature).

A plurality of sensors may be permanently deployed in the hydrocarbon well as part of its completion. The sensors provide both early detection of water breakthrough and continuous monitoring of the water fraction throughout the well lifetime. This enables taking early remedial actions in an effective way.

BRIEF DESCRIPTION OF THE DRAWINGS

To assist those of ordinary skill in the relevant art in making and using the subject matter hereof, reference is made to the appended drawings, which are not intended to be drawn to scale, and in which like reference numerals are intended to refer to similar elements for consistency. For purposes of clarity, not every component may be labeled in every drawing.

DETAILED DESCRIPTION OF THE INVENTION

Figure 1:
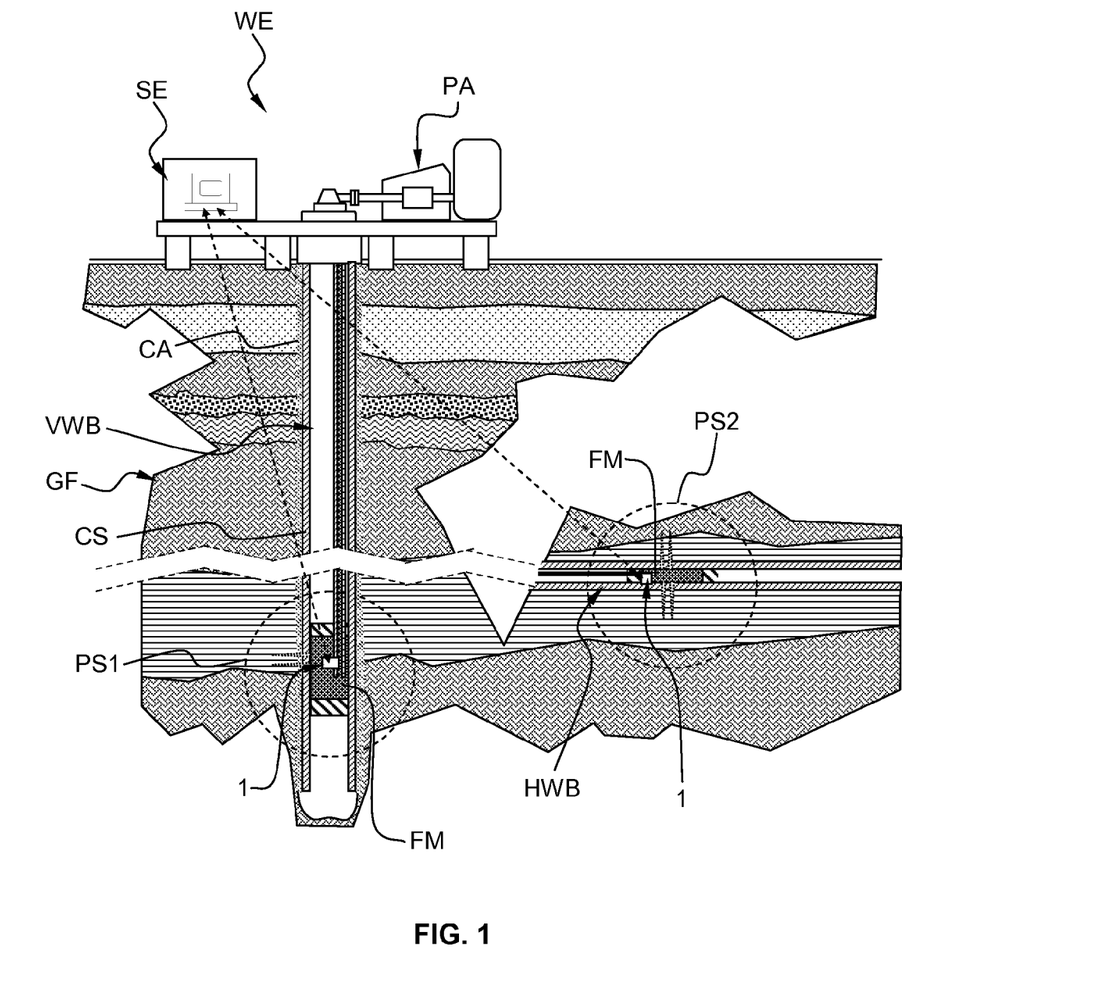
FIG. 1 schematically depicts an onshore hydrocarbon well location illustrating examples of deployment of the sensors according to an aspect of the present invention.

FIG. 1 schematically depicts an onshore hydrocarbon well location and equipments WE above a hydrocarbon geological formation GF after drilling operation has been carried out, after a drill pipe has been run, and eventually, after cementing, completion and perforation operations have been carried out. The well is beginning producing hydrocarbon, e.g. oil and/or gas. At this stage, the well bore comprises substantially vertical portion VWB and may also comprise horizontal or deviated portion HWB. The well bore VWB is either an uncased borehole, or a cased borehole comprising a casing CS and an annulus CA, or a mix of uncased and cased portions.

The annulus CA may be filled with cement or an open-hole completion material, for example gravel pack. Downhole, a first PS1 and second PS2 producing sections of the well typically comprises perforations, production packers and production tubing at a depth corresponding to a reservoir, namely hydrocarbon-bearing zones of the hydrocarbon geological formation GF. In one embodiment, one or more sensors 1 for measuring water fraction in the fluid mixture FM flowing into the cased borehole, for example in the first PS1 and second PS2 producing sections of the well (as represented in FIG. 1) or other sections of the well (not represented in FIG. 1), may be installed along the internal casing wall in contact with the fluid mixture. In the present example, the fluid mixture FM is a hydrocarbon fluid mixture that comprises a certain fraction of water (e.g. droplets of water in a continuous oil phase).

At the surface, the production tubing is coupled to appropriate surface production arrangement PA typically comprising pumping arrangement, separator and tank, etc. Surface equipment SE may comprise a computer forming a control and data acquisition unit coupled to the sensor of the present invention, and/or to other downhole sensor and/or to active completion device like valves. Surface equipment SE may also comprise a satellite link (not shown) to transmit data to a client's office. Surface equipment SE may be managed by an operator. The precise design of the down-hole producing section and surface production/control arrangement is not germane to the present invention, and thus is not described in detail hereinafter.

Figure 2:
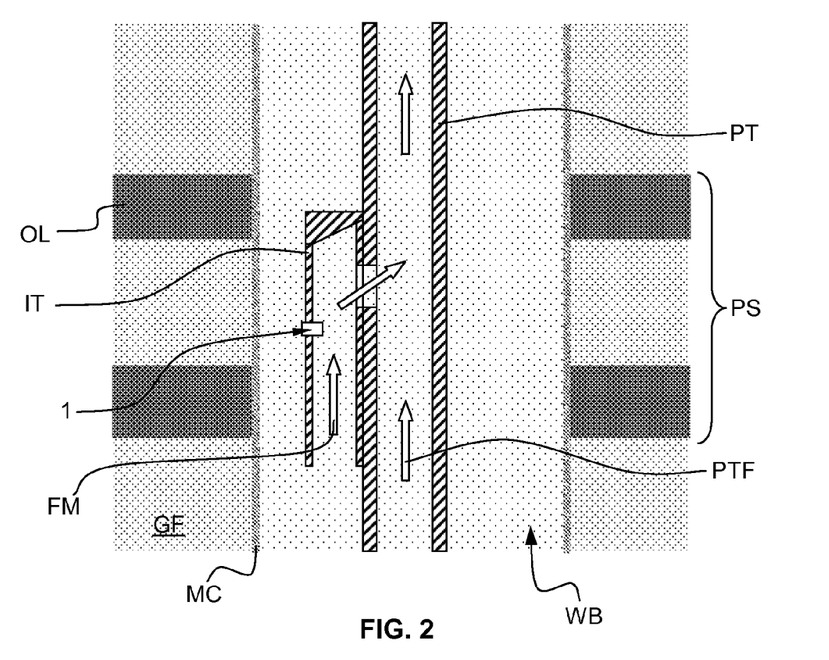
FIG. 2 is a front cross-section view in a geological formation schematically depicting a sensor of the present invention according to a first embodiment in an uncased borehole.

FIG. 2 is a front cross-section view of a geological formation GF schematically depicting a sensor 1 according to a first embodiment in an uncased vertical borehole WB. The well bore WB is an uncased borehole that may be covered by a mudcake MC. A production tubing PT directs the produced fluid mixture flow PTF towards the surface. An instrumented tubing IT is coupled outside the production tubing PT. For example, both tubing are welded together. The instrumented tubing IT may have a length ranging from a few dozen of centimeters to a meter, and a diameter of the order of a typical production tubing diameter. A first end of the instrumented tubing is opened, while the second end is closed. The instrumented tubing further comprises a lateral hole. For example, both tubings are coupled in a parallel manner and comprise a hole to communicate with each other. Thus, the fluid mixture flowing out of the producing zone PS may flow into the production tubing PT after having flown through the instrumented tubing IT. The sensor 1 of the present invention is fitted within the instrumented tubing IT. Thus, the whole volume of fluid mixture FM produced by the reservoir zone PS flowing towards the production tubing PT is measured by the sensor 1.

Figure 3:
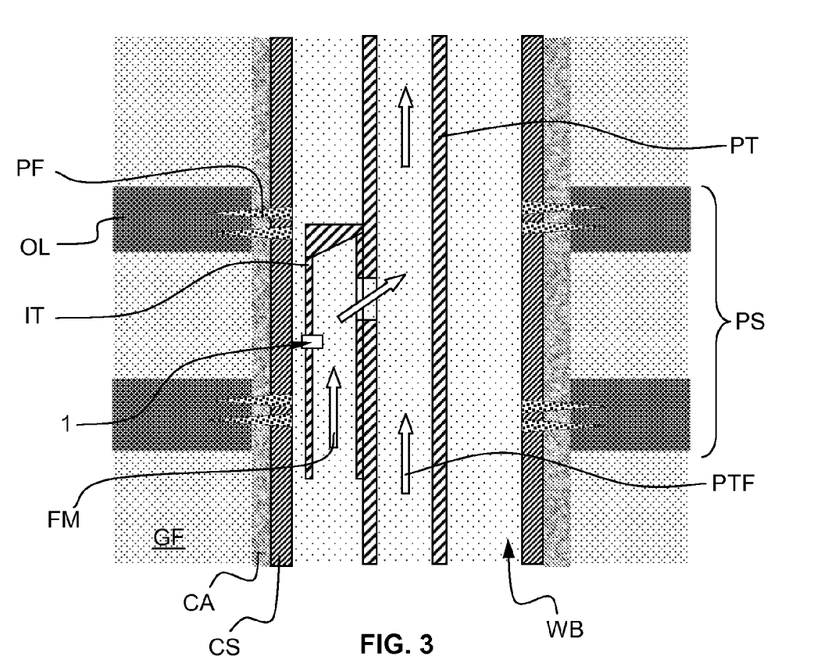
FIG. 3 is a front cross-section view in a geological formation schematically depicting a sensor of the present invention according to a first embodiment in a cased borehole.

FIG. 3 is a front cross-section view in a geological formation GF schematically depicting a sensor 1 of the present invention according to a first embodiment in a cased vertical borehole WB. The well bore WB is a cased borehole comprising the casing CS and the cemented annulus CA. The casing CS is made of conductive material, for example stainless steel or other metal alloy capable of withstanding high pressure, high temperature and corrosive environments. The annulus CA may be filled with cement or an open-hole completion material, for example gravel pack, or formation sand, or formation fluids. The fluid mixture FM produced by the reservoir zone PS flows towards the instrumented tubing through appropriate perforations PF. The other elements are identical to the ones described in relation with FIG. 2 and will not be further described.

Figure 4:
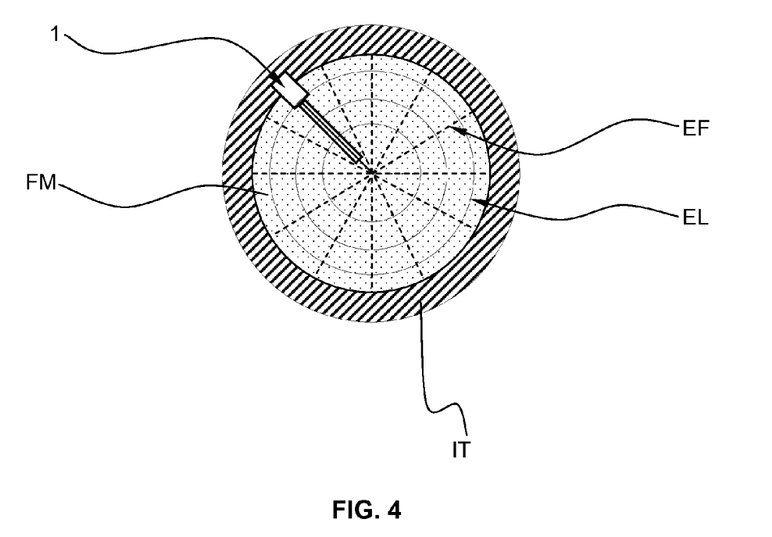
FIG. 4 is a top cross-section view in an instrumented tubing schematically depicting a sensor according to an aspect of the present invention.

FIG. 4 is a top cross-section view in the instrumented tubing IT schematically depicting the sensor 1 of the present invention. The instrumented tubing IT is made of conductive material, for example stainless steel or other metal alloy capable of withstanding high pressure, high temperature and corrosive environments. The sensor 1 is installed along the internal wall of the instrumented tubing IT. It may be fitted in a cavity of the internal wall of the instrumented tubing IT, for example screwed in a threaded cavity. Alternatively, it may be welded on the internal wall of the instrumented tubing IT. As an alternative (not shown), the probe of the sensor connects to electronic unit of the sensor that can be located outside the production tubing PT. In this case, the probe is pressure tight so that no fluid leaks outside the production tubing PT. As, the whole volume of the fluid mixture FM produced by the reservoir zone flows through the instrumented tubing IT, it is measured by the sensor 1.

Figure 5:
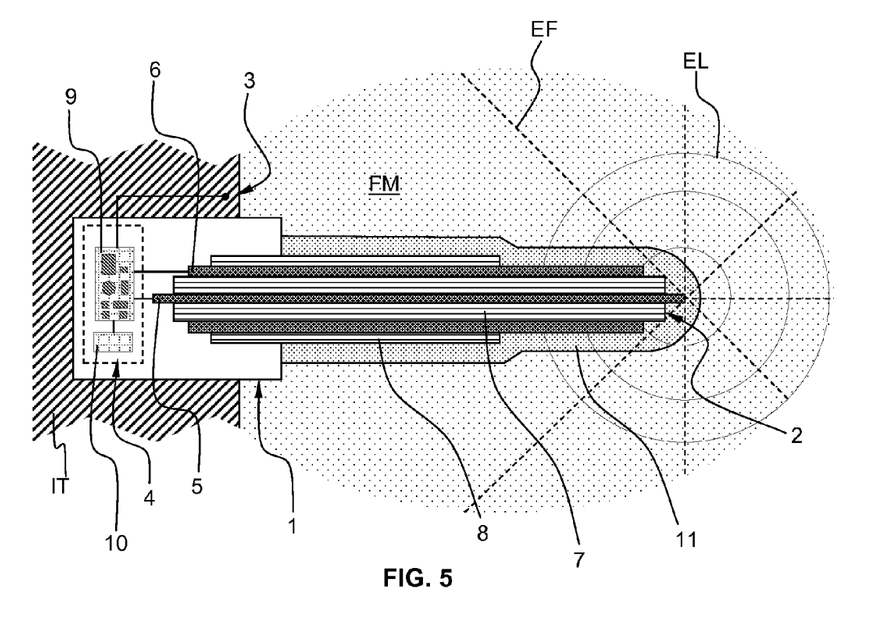
FIG. 5 is a partial front cross-section view in an instrumented tubing schematically depicting a sensor according to an aspect of the present invention.

FIG. 5 is a partial front cross-section view in an instrumented tubing IT schematically depicting in details the sensor 1. The sensor 1 comprises an active probe 2, a reference probe 3 and an electronic unit 4.

The active probe 2 is a dielectric probe. The active probe 2 comprises a first electrode 5 and a second electrode 6. The first electrode 5 is an inner electrode. The second electrode 6 is acting as an electrical shield around the inner electrode 5 such that only the end of the inner electrode 5 is sensitive to the dielectric environment within the instrumented tubing IT. The shield is maintained at the same electrical potential as the inner electrode 5 by the electronic unit. Both electrodes 5, 6 are isolated from each other by a first insulating layer 7. They are also isolated from the reference probe 3 by a second insulating layer 8. Both electrodes 5, 6 are in contact with the fluid mixture FM. The second electrode 6 forms a shielding or guard electrode. The first insulating layer 7 coats the first electrode 5 such that only the distal part of the first electrode 5 contacts the fluid mixture FM. The second insulating layer 8 coats the second electrode 6. The insulating layers are made of a ceramic or a high temperature polymer such as Peek (Trademark).

The portion of the first electrode 5 exposed to the fluid mixture is slightly shorter than the portion of the second electrode 6 (for example 10% of the full electrode length) so that the distal part of the first electrode 5 is sensitive to the capacitance of the fluid mixture FM located between the end of the first electrode 5 and the reference probe 3. The second electrode 6 acts as an electrical shielding or guard over the remaining length of the first electrode 5. Therefore the fluid capacitance is measured between the active end of the probe and the reference probe.

A protector layer cap 11 may coat the active probe 2. For long term exposure to downhole fluids in production, the cap 11 provides a protection against erosion. In particular, the erosion can be induced by small particles of sand present in the produced fluids and having high velocity. The cap 11 is made of electrically insulating material having a high degree of resistance to erosion, for example ceramic material such as Zircone. The cap 11 has low permeability to water in order to avoid electrical short-circuit between the active probe and the second electrode 6 forming a shielding conductor. Further, the effect of the thin layer cap on the measurement is small and can be removed by calibration in air or in pure oil.

The reference probe 3 is formed by the conductive wall of the instrumented tubing IT contacting the fluid mixture FM. A protector layer cap may coat the reference probe 3 in order to improve the resistance to erosion. The effect of the thin layer cap on the measurement is small and can be removed by calibration in air or in pure oil.

Advantageously, the sensor is small enough so as to form a very small restriction to the passage of the fluid mixture. Thus, minimal modification of the flow and minimal pressure loss can be achieved with the sensor of the present invention. In any case, there is no interruption of the production during the measurement.

The electronic unit 4 is coupled to the first 5 and second 6 electrodes, and also to the reference probe 3. The electronic unit ensures that the same voltage potential is applied on both electrode 5 and 6. Therefore, the second electrode 6 acts as an electrical shield and only the end of the first electrode 5 is sensitive to the capacitance of the fluid mixture FM. The electronic unit 4 comprises a capacitance module 9 measuring a capacitance between the active probe 2 and the reference probe 3. The electronic unit 4 may also comprise a transmission module 10 for transferring the measurements to the surface. The measurements may be transferred by wireless communication (acoustics or electromagnetic) or by wire between the transmission module 10 and surface equipment SE (shown in FIG. 1).

The electric field EF is radially outward from the active probe distal part, while the equipotential lines EL are concentric to the tip of the active probe. Therefore, the electric field EF interacts with all the fluid section present inside the casing.

Figure 9:
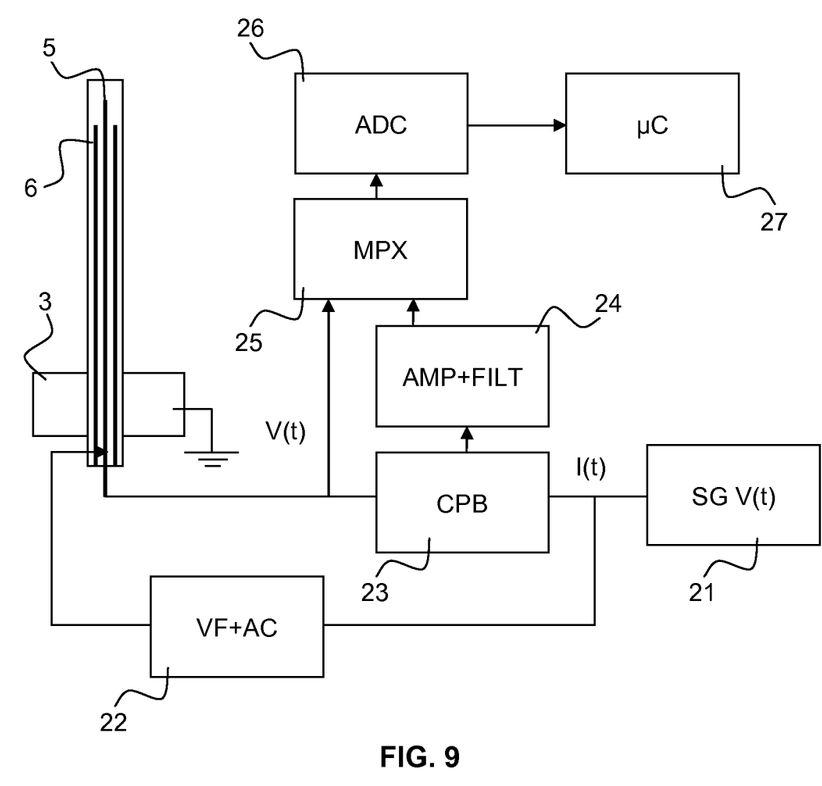
FIG. 9 schematically illustrates an example of an electronic unit for a sensor of the present invention used to measure the capacitance of the fluid surrounding the probe.

FIG. 9 schematically illustrates an example of the capacitance module 9 of the electronic unit 4 for the sensor 1 used to measure the capacitance of the fluid surrounding the probe. The capacitance module 9 comprises a signal V(t) generator 21, a voltage follower and amplifier circuit 22, a current I(t) probe 23, an amplification and filtering circuit 24, a multiplexer 25, an analog to digital converter 26, and a micro-controller 27. The signal V(t) generator 21 is coupled to the active probe 5 and also to the voltage follower and amplifier circuit 22. The current I(t) probe 23 is coupled to the active probe 5 and to the amplification and filtering circuit 24. Both the current I(t) and the voltage V(t) are delivered to the multiplexer 25. The multiplexer 25 is coupled to the analog to digital converter 26 which is coupled to the micro-controller 27. The micro-controller 27 processes the digital signal for computation of the capacitance as explained hereinafter.

Thus, the sensor 1 can measure the water holdup, namely the volume fraction of water in the produced hydrocarbon fluid mixture FM flowing into the casing. The water holdup is determined by measuring the capacitance between the active probe and the inner wall of the casing acting as reference probe.

The measured capacitance value is a function of the dielectric constant of the fluid surrounding the probe and the geometry of the probe and casing. Since the dielectric constants for oil and water are known, the volume fraction of water can be calculated as described hereinafter.

As a first approximation, the capacitance value is given by the following equation for capacitor having cylindrical geometry:

$$C = \frac{1 * 2 * \pi * \varepsilon_0 * \varepsilon_f}{\ln[a/b]}$$

where:
l is an active probe length exposed to the fluid mixture;
$\varepsilon_0$ is a vacuum permittivity;
$\varepsilon_f$ is a fluid mixture dielectric constant;
b is an active probe radius; and
a is a reference tubing internal radius.

The dielectric constant $\varepsilon_f$ of the fluid mixture surrounding the active probe can be inferred from the capacitance measurement C.

As the capacitance measurement accounts for the whole cross-section area of the casing, this measurement is sensitive to all the fluid volume present inside the instrumented tubing.

Prior to the deployment of the sensor, the sensor together with its associated electronic unit can be calibrated in air or in pure oil which dielectric constant $\varepsilon_{ref}$ is well known. Thus, the geometrical parameters in capacitor equation can be estimated.

$$C_{cal} = \frac{1*2*\pi*\varepsilon_0*\varepsilon_f}{\ln[a/b]}$$

The dielectric constant of the fluid mixture is therefore given by:

$$\varepsilon_f = \frac{C}{C_{cal}}$$

The water fraction can be inferred from the measurement of the fluid dielectric constant. In mixed oil and water conditions where the continuous phase is oil, the variation of the fluid dielectric constant $\varepsilon_f$ versus water fraction $H_w$ is given by following formula established by Bruggeman:

$$\varepsilon_f = \frac{\varepsilon_{oil}}{(1 - H_w)^3}$$

The Bruggeman formula is based on the assumption that water is present in the form of small droplets with random diameter and distribution. This model fits very well with experimental results as long as the fluid has an electrically insulating continuous phase (e.g., oil phase). The model is valid if the measurement frequency is below 100 kHz.

Since the oil dielectric constant $\varepsilon_{oil}$ can be measured separately or assumed to be constant versus reservoir production time, the water holdup/fraction $H_w$ can be derived from $\varepsilon_f$ by using the Bruggeman formula. Obviously, the oil fraction can also be deduced. The oil dielectric constant $\varepsilon_{oil}$ may vary according to the hydrocarbon type. However, the variation range is limited, e.g. the range of variation is about [1.7-2.2]. Further, it is to be noted that oil dielectric constant $\varepsilon_{oil}$ is quite stable versus temperature.

The above described measurements, equations and approximations apply for a fluid mixture comprising small amount of water relatively to the volume of oil. In case, the water holdup is above a determined threshold, which may vary between 30% to 60% of water according to the flow conditions, the water might become a continuous phase and a continuous electrical path is established from the active probe to the internal wall of the instrumented tubing. Practically, under this condition, a short circuit is measured by the active probe. Above this threshold, the water cut cannot be measured, but a clear indication of water presence is obtained. This information helps managing the production operation, for example a valve may be closed to choke the production zone where water-breakthrough has been detected.

Figure 6:
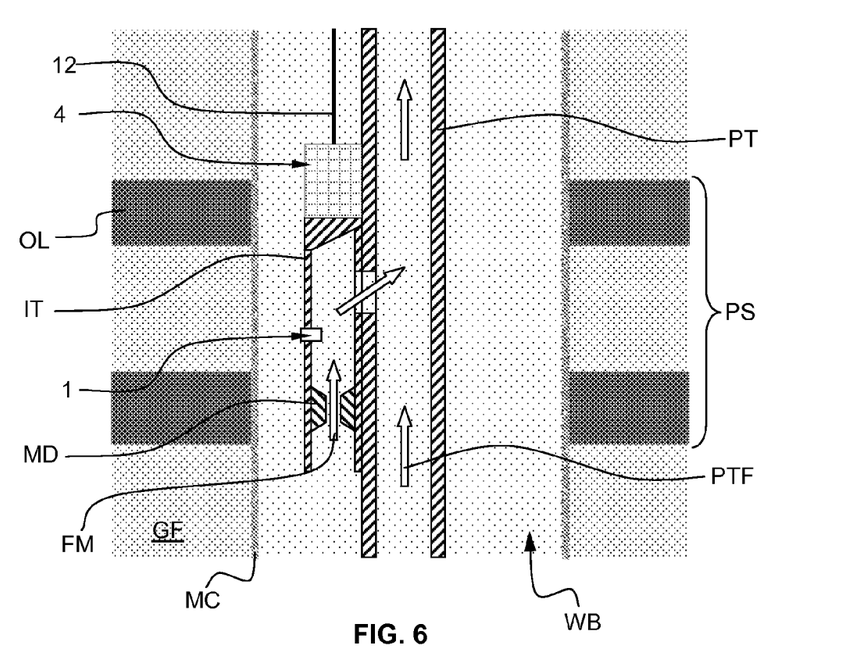
FIG. 6 is a front cross-section view in a geological formation schematically depicting a sensor of the present invention according to a second embodiment in an uncased borehole.

FIG. 6 is a front cross-section view in a geological formation GF schematically depicting the sensor 1 of the present invention according to a second embodiment in an uncased borehole.

The producing hydrocarbon well WB comprises an uncased borehole in a geological formation GF comprising at least a layer of oil OL. The wall of the borehole may comprise a mudcake MC. It further comprises a completion consisting of a production tubing PT. It may further comprise a packer and a series of perforations in a cased portion of the borehole (not shown). A produced hydrocarbon fluid mixture PTF flows towards the surface through the production tubing PT. In the production zone PS, the instrumented tubing IT comprising the sensor 1 is coupled to the production tubing PT. The hydrocarbon fluid mixture flowing from the production zone PS flows into the production tubing through the instrumented tubing IT.

Figure 7:
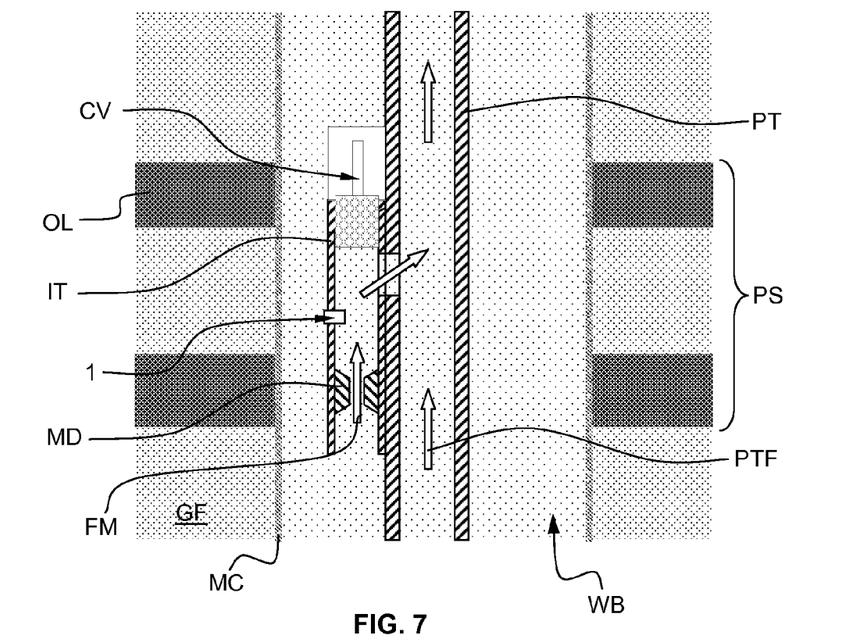
FIG. 7 is a front cross-section view in a geological formation schematically depicting a sensor of the present invention according to a third embodiment in an uncased borehole.

The instrumented tubing IT may further comprise a mixing device MD in order to properly mix the fluid mixture FM before contacting the active probe of the sensor 1. The mixing device MD may be for example a helix (not shown) or a restriction to the flow cross-section such as a Venturi (as depicted in FIGS. 6 and 7). Advantageously, the mixing device is positioned upstream of the sensor such as to achieve a proper mixing of the fluid mixture ahead of the probe.

When a proper mixing is achieved, all the phases of the fluid mixture move at the same velocity inside the casing. Therefore, the water holdup/fraction measurement is equivalent to the water cut. According to this alternative embodiment, the sensor can provide a robust measurement of the water cut.

The electronic unit 4 is coupled to surface equipment via an electrical cable 12 providing power and communication. The other elements of the instrumented tubing and the sensor are identical to the ones described in relation with FIG. 2 (first embodiment) and will not be further described.

FIG. 7 is a front cross-section view of a geological formation GF schematically depicting a sensor 1 according to a third embodiment in an uncased borehole. In this embodiment, the instrumented tubing IT further comprises a control valve CV to choke the hydrocarbon fluid mixture production of the producing zone PS. The sensor 1 is coupled to the control valve CV in order to form a production controlling system of the associated producing zone PS. In a preferable aspect of the present embodiment, the sensor controls the operation of the valve as a function of the measured water holdup/fraction in the fluid mixture FM produced by the producing zone PS. In particular, the control valve CV may be closed and the production of the specific producing zone PS may be interrupted when the water holdup/fraction exceeds a determined water fraction threshold value. However, the control valve CV may be controlled in any number of manners, such as by an operator at surface or independently based on a timer.

The other elements of the instrumented tubing and the sensor are identical to the ones described in relation to the FIG. 2 embodiment and will not be further described.

Figure 8:
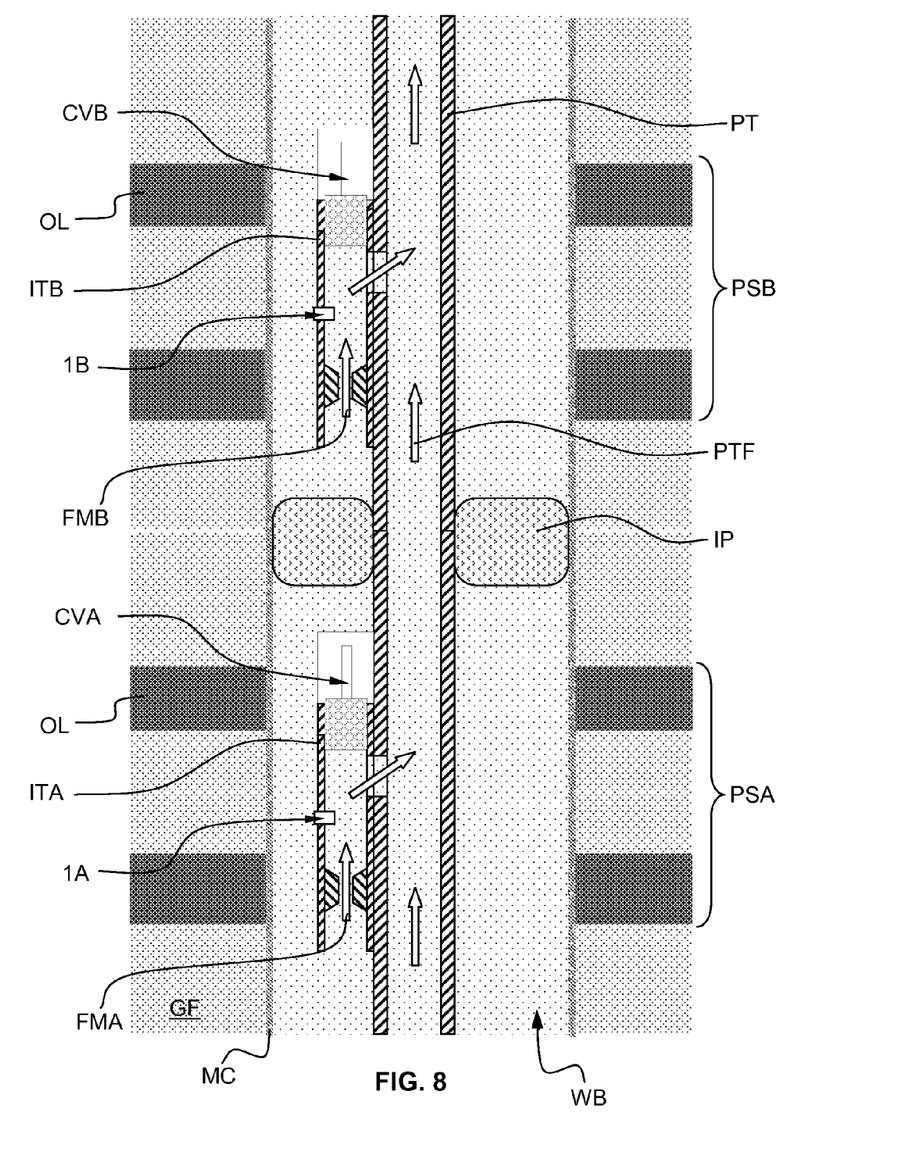
FIG. 8 is a front cross-section view in a geological formation schematically depicting two sensors of the present invention according to the second embodiment associated to two different producing zones in an uncased borehole.

FIG. 8 is a front cross-section view of a geological formation GF schematically depicting two sensors 1A, 1B according to the second embodiment associated to two different producing zones PSA, PSB in an uncased borehole. The two producing zones PSA, PSB are separated from each other by an insulation packer IP. Though FIG. 8 only depicts two sensors, one associated to a first production zone PSA and one associated to a second production zone PSB, even more sensors may be deployed (not shown). In particular, a plurality of sensor can be permanently deployed in different zones along the producing well such as to form an array of sensors. The array of sensors allows identifying how water entries are distributed along the well.

It should be appreciated that embodiments of the present invention are not limited to onshore hydrocarbon wells and can also be used offshore. Furthermore, although some embodiments have drawings depicting a vertical well-bore, said embodiments may also apply to a horizontal or deviated well-bore. All the embodiments of the present invention are equally applicable to cased and uncased borehole. Although particular applications of the present invention relate to the oilfield industry, other applications to other industry, e.g. the water industry or the like also apply.

Moreover, it should be appreciated that while the present invention has been described with reference to exemplary embodiments and implementations thereof, the present invention is not to be limited by or to such exemplary embodiments and/or implementations. Rather, the systems and methods of the present invention are susceptible to various modifications, variations and/or enhancements without departing from the spirit or scope of the present invention. Accordingly, the present invention expressly encompasses all such modifications, variations and enhancements within its scope.

Any reference sign in a claim should not be construed as limiting the claim. The word "comprising" does not exclude the presence of other elements than those listed in a claim. The word "a" or "an" preceding an element does not exclude the presence of a plurality of such element.

What is claimed is:

1. A sensor for measuring water fraction in a fluid mixture, wherein the sensor comprises:
    an active probe having a first electrode and a second electrode extending inwardly from a wall forming a conductive tubing through which the fluid mixture flows in a borehole, the first electrode and the second electrode being isolated from each other by a first insulating layer, the second electrode being positioned around the first electrode to provide an electric shielding over a portion of the first electrode, the first and second electrodes being in contact with the fluid mixture;
    a reference probe formed from an internal wall of the conductive tubing contacting the fluid mixture and isolated from the first electrode and the second electrode of the active probe by a second insulating layer; and
    an electronic unit coupled to the first and second electrodes, and to the reference probe, the electronic unit having a capacitance module for measuring a capacitance between the active probe and the reference probe.

2. The sensor of claim 1, wherein the first and second insulating layer coats the first and second electrode, respectively, such that the first and second electrodes contacts the fluid mixture at a distal part of the first and second electrodes.

3. The sensor of claim 1, wherein the active probe and/or the reference probe is coated by a protector layer cap.

4. The sensor of claim 1, wherein the fluid mixture is a hydrocarbon fluid mixture.

5. The sensor of claim 1, wherein the sensor is coupled to a mixing device for mixing the fluid mixture prior to being in contact with the active probe of the sensor.

6. The sensor of claim 5, wherein the mixing device is a helix or a restriction to the flow cross-section forming a Venturi throat.

7. The sensor of claim 1, wherein the electronic unit further comprises a transmission module to transfer measurements to surface equipments.

8. The sensor of claim 1, wherein the conductive tubing is further defined as an instrumented tubing connectable outside a production tubing, a first end of the instrumented tubing being open, a second end of the instrumented tubing being closed, and wherein the instrumented tubing comprises a lateral hole adapted to direct the fluid mixture into the production tubing.

9. A production controlling system of a producing zone of a hydrocarbon well, the system comprising:
    a production tubing;
    an instrumented tubing mounted externally of the production tubing, the instrumented tubing having a conductive tubing in fluid communication with an interior of the production tubing;
    a sensor mounted to the conductive tubing to measure water fraction in a fluid mixture flowing from the conductive tubing to the interior of the production tubing within a borehole, the sensor comprising:
        an active probe extending into an interior of the conductive tubing, the active probe having a first electrode and a second electrode isolated from each other by a first insulating layer, the second electrode providing an electric shielding over a portion of the first electrode, the first and second electrodes being exposed to the fluid mixture;
        a reference probe formed from an internal wall of the conductive tubing contacting the fluid mixture and isolated from the first electrode and the second electrode of the active probe by a second insulating layer; and
        an electronic unit coupled to the first and second electrodes, and to the reference probe, the electronic unit having a capacitance module for measuring a capacitance between the active probe and the reference probe; and
    a valve to choke the producing zone, wherein the valve being coupled to the sensor, and wherein the sensor being adapted to operate the valve as a function of the measured water fraction in the fluid mixture produced by the producing zone and a threshold water fraction value.

10. A method of measuring water fraction in a fluid mixture flowing in a conductive tubing within a borehole, the method comprising:
    measuring the water fraction with a sensor having an active probe extending inwardly from a wall of the conductive tubing to an interior of the conductive tubing to establish contact with the fluid mixture;
    coupling the sensor to the conductive tubing such that an internal wall surface of the conductive tubing forms a reference probe which is in contact with the fluid mixture; and
    measuring a capacitance between the active probe and the reference probe as the fluid mixture is flowed along the conductive tubing within the borehole.

11. The method of claim 10, wherein the fluid mixture is a hydrocarbon fluid mixture.

12. The method of claim 11, wherein the water fraction in the fluid mixture is calculated by determining the dielectric constant of the fluid mixture surrounding the active probe from the capacitance measurement C by using the formula:

$$C = \frac{l * 2 * \pi * \varepsilon_0 * \varepsilon_f}{\ln[a/b]}$$

wherein:
l is an active probe length exposed to the fluid mixture;
$\varepsilon_0$ is a vacuum permittivity;
$\varepsilon_f$ is a fluid mixture dielectric constant;
b is an active probe radius; and
a is a reference tubing internal radius.

13. The method of claim 12, wherein the water fraction $H_w$ in the fluid mixture is calculated by using the formula:

$$\varepsilon_f = \frac{\varepsilon_{oil}}{(1-H_w)^3}$$

wherein $\varepsilon_{oil}$ is an oil dielectric constant.

14. Application of the method according to claim 10 to the control of production of a hydrocarbon reservoir, comprising the steps of:
   measuring the water fraction in the fluid mixture of a producing zone; and
   operating a valve to choke the producing zone when the measured water fraction in the fluid mixture exceeds a threshold value.

15. The method of claim 1, wherein the first and second electrodes are in contact with the fluid mixture such that the portion of the first electrode exposed to the fluid mixture is shorter than the portion of the second electrode exposed to the fluid mixture.

\* \* \* \* \*